United States Patent [19]
Ahmad et al.

[11] Patent Number: 5,192,686
[45] Date of Patent: Mar. 9, 1993

[54] RHIZOSPHERE-COMPETENT TRICHODERMA STRAINS

[76] Inventors: Syed J. Ahmad, Tahir Ahmadiyya Muslim High School, Mansakonko (L.R.D.) The Gambia, South Africa; R. Ralph Baker, 1216 Southridge, Ft. Collins, Colo. 80421

[21] Appl. No.: 512,748

[22] Filed: Apr. 20, 1990

Related U.S. Application Data

[63] Continuation of Ser. No. 72,347, Jul. 10, 1987, abandoned.

[51] Int. Cl.$^5$ .................. C12N 1/14; C12N 15/00; A01N 63/00; A01C 1/06
[52] U.S. Cl. ........................ 435/254; 435/172.1; 435/945; 424/93 B; 424/93 Q; 47/57.6
[58] Field of Search ............ 435/254, 945, 172.1; 424/93, 93 B, 93 Q; 47/58, 57.6

[56] References Cited

PUBLICATIONS

Papavizas et al. 1982. Phytopathology 72(1):126-132.
Sunar et al. 1971. Indian J. Agric. Sci. 41(1):29-37.
Ahmad et al. 1985. Phytopathology 75(1):1302.
Cuskey S. M., Montenecourt, B. S., and Eveleigh, D. E. 1983. Screening for cellulolytic. pp. 31-48 in. Liquid Fuel Developments. Ed. D. L. Wise, pp. 31-47. CRC Press, Boca Raton, Fla. 210 pp.
Ghose, T. K. 1987. Measurement of cellulose activities. Pure and Appl. Chem. 59:257-268.
Sivan, A., and Harmon, G. E. 1991. Improved rhizosphere competence in a protoplast fusion progeny of Trichoderma harzianum. Journal of General Microbiology (1991), 137, 0000-0000.
Mendez-Castro and Alexander, Method for Establishing a Bacterial Inoculum on Corn Roots Eviron, Microbiol 45:254-258 (1983).
Garrett S. D. Pathogenic Root Infected Fugi, Cambridge University Press (1970) Foster and Rovira & Cock, Ultrastructure of the Root Soil Interface, AM. Phytopath, Soc. St. Paul, Minn. (1983), page v.
Ahmad and Baker, Competitive Saprophytic Ability and Celluloytic Activity of Rhizosphere-Competent Mutants of Trichoderma harzionum; Phytopathology 77:358 (1987).
Ahmad and Baker, Rhizosphere-Competent in Trichoderma harzanium Phytopathology (Feb. 1987) vol. 77:182-189.
Foster et al., *Ultrastructure of Root-Soil Interference*, Am. Phytopath. Soc. St. Paul, Minn. (1983).
Lifshitz et al., *Decrease in Incidence of Rhizoctonia Preemergence Damping-Off by Use of Integrated Chemical and Biological Controls, Plant Diseases, May 1985: 431.*
Chang et al., *Increased Growth of Plants in Presence of Biological Control Agent,* Trichoderma harzianum for increased plant growth. Plant Dis. 70:145 (1986).
Papavizas, G. C. Trichoderma and Gliocladium: Biology, Ecology and Potential For Biocontrol Ann. Rev. Phytopathology 23:23-54 at page 35, 1985.
Papavizas, G. C., Survival of Trichoderma harzianum in Soil and in Pea and Bean Rhizospheres: Ecology and Epidemiology, vol. 72, No. 1, 121-125 at p. 124 (1982).
Ahmad, J. S. & Baker, Ralph, Rhizosphere-Competence of Benomyl-Tolerant Mutants of Trichoderma spp., Can. J. Microbiol 34:694-696 (1988).
Ahmad, J. S., & Baker, Ralph, Growth of Rhizosphere-Competent Mutants of Trichoderma harzianum on Carbon, Can. J. Microbiol. 34:807-814.

*Primary Examiner*—David T. Fox
*Attorney, Agent, or Firm*—Dorr, Carson, Sloan & Peterson

[57] ABSTRACT

A rhizosphere-competent *Trichoderma polysporum*, (ATCC 20852) and a rhizosphere-competent *Trichoderma viride* (ATCC 20853) are described. They are respectively, mutants of rhizosphere-incompetent *Trichoderma polysporum* ATCC 20475 and rhizosphere-incompetent *Trichoderma viride* ATCC 20476. The rhixosphere-competent strains are particularly effective biocontrol agents for plant and/or tree diseases associated with various fungi e.g., Pythium spp., Sclerotium, spp., *Rhizoctonia solani* and basidiomycetes such as *Chondrostereumm purpureum*.

2 Claims, 3 Drawing Sheets

RHIZOSPHERE-COMPETENT TRICHODERMA STRAINS

BACKGROUND OF THE INVENTION

Statement of Co-Pendency

This patent application is a continuation application of U.S. patent application Ser. No. 72,347 entitled "Rhizosphere-Competent Trichoderma Strains" filed Jul. 10, 1987, now abandoned.

FIELD OF THE INVENTION

This invention generally relates to new biotypes of soilborne biocontrol agents. More specifically it relates to rhizosphere-competent biocontrol agents. The term "rhizosphere competence" has been employed to describe an attribute of rhizobia characterized by their consistent association with legume root nodules. For the purpose of this patent application, the term rhizosphere-competence is used to describe the ability of a microorganism to grow and function in the developing rhizosphere. In application, this means that the microorganism can be placed on the seed, it can grow and it can colonize the rhizosphere of the developing root.

2. Description of the Prior Art

The protection of plants from infection by soilborne fungal and bacterial pathogens by use of antagonistic microorganisms is well known to the art. For example, it is known that various Trichoderma spp. such as *Trichoderma harzanium* Rifai act as biological control agents against certain plant diseases. Nonetheless, use of Trichoderma spp., as biocontrol agents has been rather limited. This is mainly because seed treatment with Trichoderma spp. generally does not provide continued protection for the emerging root system of the maturing plant. Such seed treatment does serve to reduce pre-emergence damping-off, but the root system is left unprotected. It is generally believed that this failure to protect the root system is because Trichoderma spp. are not rhizosphere-competent; see for example, Papavizas, G. C., Phytopathology 72: 121-125 (1982) and Chao, W. L., et al., Phytopathology 76: 60-65 (1986). Therefore, a need for rhizosphere-competent Trichoderma spp., is manifest.

The need for rhizosphere-competent in bacterial biocontrol agents has been partially met; see for example: Mendez-Castro, F. A. and Alexander, M., *Method For Establishing A Bacterial Inoculum On Corn Roots*, Appl. Eviron., Microbiol. 45: 254-258 (1983). A similar plant protection strategy has been applied to fungal biocontrol agents (Ahmad, J. S., and Baker, R., Rhizosphere competence of *Trichoderma harzanium*, Phytopathology 77: 182-189 (1987)). This work indicates that when benomyl-tolerant mutants of *Trichoderma harzanium* Rifai were applied to seeds, the roots became colonized. However, the reason or reasons as to why such mutants are rhizosphere-competent, were not apparent. It seems that many of the results obtained from following this research strategy were inconsistent and/or in conflict with what was then known about rhizosphere-competence. For example, it should be noted that the Papavizas article previously cited discloses the use of benomyl tolerant isolates of *T. harzanium*, obtained by ultraviolet light irradiation, to test for rhizosphere-competence of bean and pea seedlings. However, Applicants found that ultraviolet mutants, tolerant to benomyl, were not rhizosphere-competent. Moreover, reports by other workers (see for example, Garrett, S. D., Pathogenic root-infected fungi, Cambridge University Press (1970)) postulated the theory that the share of a substrate obtained by any particular fungal species is determined partly by its intrinsic competitive saprophytic ability and partly by the balance between its inoculum potential and that of competing species. This report also theorized that production of, and tolerance to, antibiotics is another important attribute of successful rhizosphere fungi.

All of these theories were however, to some degree, inconsistent with the results of Applicants' rhizosphere competence tests. For example, Applicants found that both the mutants and the wild types had the same population density when applied to seeds. Moreover, none of Applicants' mutant strains have antibiotic activity in vitro except for a routing factor seen in the hyphal cytoplasm, at microscopic levels affecting Pythium spp. In trying to reconcile these theoretical and/or evidentiary conflicts, as well as those relating to the nature of the plant root surfaces themselves (see for example, Foster, R. C., Rovira, A. D., and Cock, T. W., *Ultrastructure of the Root-Soil Interface* Am. Phytopath. Soc., St. Paul, Minn. (1983), Applicants have developed two particularly effective rhizosphere-competent strains of Trichoderma.

SUMMARY OF THE INVENTION

These particularly useful Trichoderma species are *Trichoderma polysporum*, ATCC number 20852 and *Trichoderma viride*, ATCC number 20853. They are particularly useful in controlling diseases caused by Phythium spp., Sclerotium spp., and *Rhizoctonia solani* in such varied plants as beans, maize, tomato, radish, cucumber, wheat, barley, lettuce and carnations. Applicants also have found that N-methyl-N-nitro-N-nitrosoguanidine was a particularly useful mutagenic chemical in producing Trichoderma species which possess the desired rhizosphere-competence characteristic. Other useful mutagenic agents would include, but not limited to ultraviolet light and x-ray radiation. These Trichoderma (e.g., the *Trichoderma polysporum* and *Trichoderma viride* species disclosed herein) are particularly effective when they are mutated for both rhizosphere-competence and benomyl tolerance. Ideally the herein disclosed strains are grown in a nutrient medium where cellulose represents a major part of the microorganisms source of carbon, or more preferably its only source of carbon. Representative sources of carbon would include, but not be limited to carboxy-methyl-cellulose, cotton linters, solka floc, and Sigma Cell 20 (Sigma Chemicals, St. Louis).

The most effective cellulose producing strains of Trichoderma species thus far produced by this path of Applicants' work have been deposited with the American Type Culture Collection, 12301 Parklawn Drive, Rockville, Md. 20852, under the following designations.

| Trichoderma spp. Designation of Novel Strain | Applicants' Designation | Parent T. spp. | ATCC |
|---|---|---|---|
| polysporum 20852 | T.P. 18 | ATCC 20475 | ATCC |
| viride | T.V. 62 | ATCC 20476 | ATCC |

| Trichoderma spp. Designation of Novel Strain | Applicants' Designation | Parent T. spp. | ATCC |
|---|---|---|---|
| | | | 20853 |

In keeping with the provisions of the directive found on page 638, volume 886 of the Official Gazette of the United States Patent Office, progeny of each and every novel strain will be made available during the pendency of this patent application to anyone determined by the Commissioner of Patents and Trademarks to be entitled thereto under 37 CFR Sec. 1.14 and 35 USC 12.2. All restrictions on the availability to the public of progeny of each and every such novel strain will be irrevocably removed upon the granting of a patent of which these novel strains are subject.

DESCRIPTION OF THE DRAWINGS

FIG. 2A shows the result for *T. polysporum* ATCC 20475 and ATCC 20853.

DESCRIPTION OF THE PREFERRED EMBODIMENTS

Figure 1:
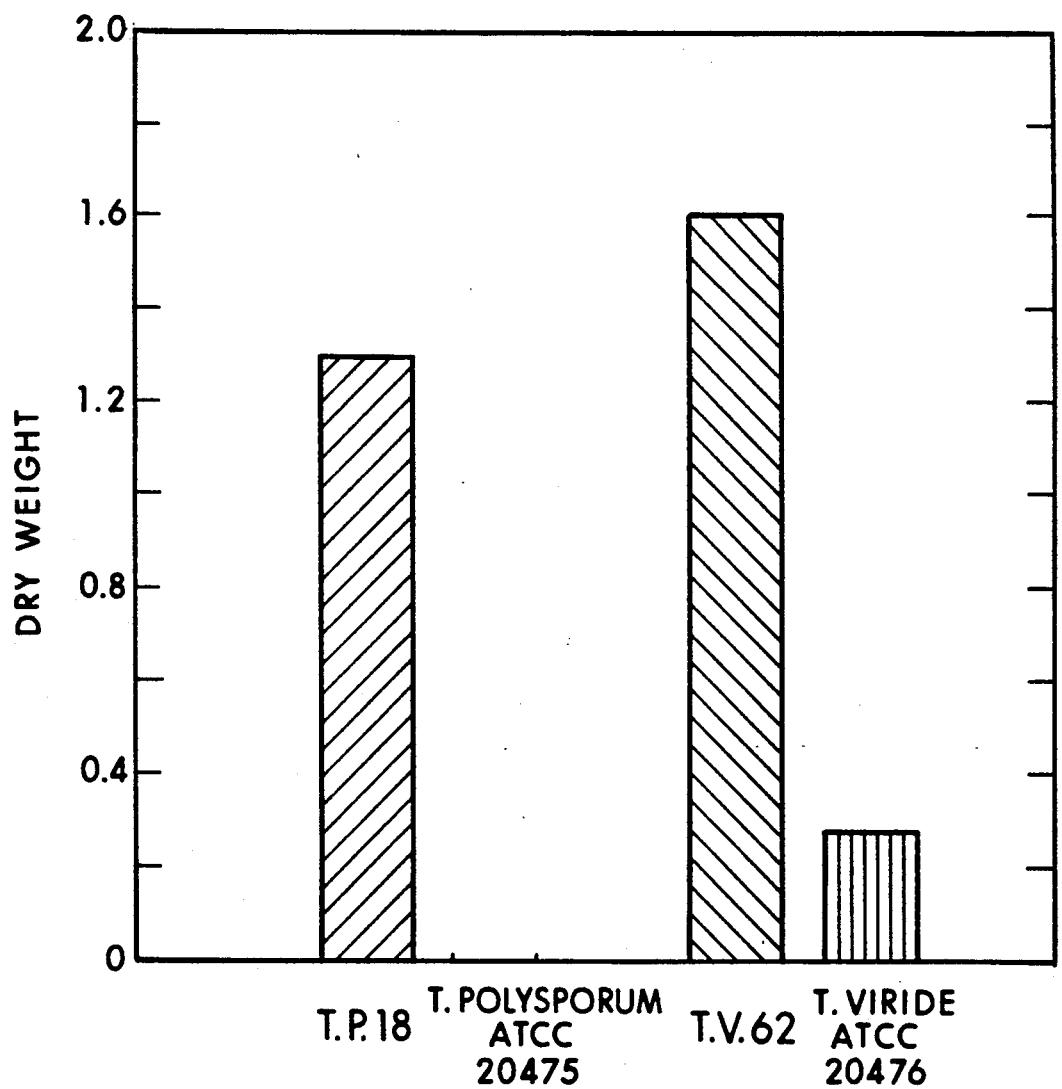
FIG. 1 is a bar graph depicting the dry weight of mycelium of strains of two Trichoderma spp. grown for 6 days in Czapek Dox broth with 37. Cellulose as the sole source of carbon.

Test for Rhizosphere Competence. Various methods have been employed to test rhizosphere competence. These were primarily based on a comparison of the number of colony forming units ("cfu") of microorganisms in the soil associated with roots when compared to population densities in non-rhizosphere soil. The rhizosphere competence assay used in this research effort was also directed toward improving measurement in time and space of the activity of potential rhizosphere inhabitants. Certain criteria were demanded by the experimental questions to be examined. Quantitative analysis of population densities at each depth of root was also necessary. No water was added during incubation obviating the possibility of propagules being washed into the rhizosphere. To test whether the agent introduced from a seed into the rhizosphere could compete under typical ecological conditions, raw soil was used. Hence, the resulting system allowed rhizosphere competence to be measured on the basis of cfu/,g or g of rhizosphere soil as a function of root depth.

The nature and quantity of root exudates have been analyzed in the past in axenic systems by use of perfusion and filter paper absorption techniques. Since such analysis often is obtained under gnotobiotic conditions, it is difficult to extrapolate such findings into the ecological conditions present in the rhizospheres of plants growing in raw soil. To overcome this objection, bioassays relating magnitudes of microbial population densities in the rhizosphere compared with non-rhizosphere soil were developed (R/S ratio). Such analyses are subjected to many variables and, at best, provide only a relative force assay of the activity of the total biomass about the root. The rhizosphere competence assay provided a quantitative measurement of a specific rhizosphere-competent microorganism at the root tip where exudates are in relatively high concentration. In more mature portions of the root however, interpretations based on population densities are confounded by maturation of the agent resulting in propagule production, various interaction leading to auto-or heterolysis, and/or changes in characteristics of the substrates provided by senile tissues of the root. Nevertheless, the rhizosphere competence assay provides the best bioassay yet developed for the rhizosphere nitrous statues at root tips. It has potential for use in a wide variety of experimental problems related to ecological and nutritional interactions in the rhizosphere.

The Trichoderma spp. disclosed herein were tested for rhizosphere competence by coating seeds with the respective isolates and following population densities of the fungus to a root depth of 8 cm. Both grew to a depth of 8 cm. Again, Trichoderma spp. which are benomyl tolerant as well as rhizosphere competent are preferred embodiments of this invention. Our particular rhizosphere-competence assays were conducted as follows. Polypropylene centrifuge tubes (28.6 by 103.6 mm) were sliced longitudinally into two halves. Each half was filled with moistened soil ($-3$ bars) and pre-incubated for 48 hours in plastic bags. One treated seed was placed on the half-tube 1 cm below the rim. The unseeded half-tube was placed on the first half and secured with rubber bands. Tubes were completely randomized and lots in portions of six each were placed vertically in 10 cm diameter plastic pots. Soil, previously moistened to $-0.03$ bars and of the same pH as in the tubes, was added to the pots so that the length of the tube was surrounded by the soil, with the top 1 cm of each tube being uncovered. No water was added to the tubes or the pots after the seeds were sown. Pots were covered with plastic bags to maintain constant metric potential leaving enough space above the tubes for the plants to grow. Pots were placed under constant illumination supplied by 10 white, 40-watt, 120 cm long fluorescent lamps (approximately 5000 lux), at desired temperatures.

After 8 days, tubes were removed from the pots. After the unseeded half of a tube was carefully lifted, the roots in the seeded half, starting from the crown, were excised in 1 cm segments with a sterile scalpel. The scalpel was flamed between cuts. After loosely adhering soil was shaken off, root segments with their adhering rhizosphere soil they were air dried under a 100-watt lamp for 30 minutes. Each unit was weighed and transferred to a 20 ml glass vial containing 1 ml sterile distilled water. The contents of the vial were stirred vigorously with a sterile spatula. The colony forming units (cfu) of each of the two Trichoderma species contained in the respective rhizosphere soils at each cm of roots were determined by plating a series of 10-fold dilutions from a vial of Trichoderma selective medium. Root segments were removed from the dilution flask, blotted on paper towel and weighted to determine the dry weight of rhizosphere soil removed through washing. Plates were incubated at 25° C. for 5 days. Counts of Trichoderma cfu per mg rhizosphere soil for each root segment were made with six replicates per treatment. All experiments were repeated twice.

Statistical analysis. The date for weight of mycelium and RC index was subjected to one way analysis of variance and the means were separated with an FLSD (P=0.05).

Materials

Soil. Nunn sandy loam was used in these investigations. Water content of 43.2 kg portions was adjusted to −0.03 bars and the soil was stored for 48 hours before use. The soils had the following characteristics: pH 7.0; conductivity 0.4 mmhos; lime low; organic matter 1.4%, $NO_3$-N 1 hg/g, P 9 mg/g; K 198 mg/g, Zn 0.5 mg/g and Fe 3.2 mg/g. Its pH was measured by the $CaCl_2$ method. Conidia of *Trichoderma polysporum* ATCC 20475 and *Trichoderma viride* ATCC 20476 were exposed to 100 mg/ml of N-methyl-N-nitro-N-nitrosoguanidine (Sigma Chemicals Co., St. Louis, Mo.) for 30 minutes. The conidia were centrifuged at 2500 g for 15 minutes and resuspended in sterile water three times. Seeds of cucumber (*Cucumis sativus* L. "straight Eight"), were surface disinfected for 10 minutes in 1.1% sodium hypochlorite solution an 5% ethanol, washed in distilled water, and air dried. Seeds were treated with conidial suspensions of each of the two Trichoderma spp. in water containing 2% (v/w) Pelgel (The Nitragen Co., Milwaukee, Wisc.) as spreader or sticker. Conidial density was adjusted to $10^6$ per seed. Controls were treated with Pelgel alone.

Growth of Trichoderma spp. in liquid culture. Strains of each of the two subject Trichoderma spp. were grown in 250 ml Erlenmeyer flasks containing 50 ml Czapek Dox broth on a rotary shaker at 100 rpm at 26° C. for 6 days. Cellulose (Sigma Cell 20) was used as the sole source of carbon. Each flask was seeded with a 4 mm diameter disk of PDA on which the strains had been grown for 2 days. After 6 days the hyphal mat was removed aseptically and dried for 2 days at 60° C. to obtain the weight of mycelium. There were six replicates per strain.

Rhizosphere competence (RC) index. Rhizosphere competence index (RC index) for each strain was developed from the data by use of the equation:

$$RC \text{ index } \sum_{n}^{i=1} = [\log (P_i \text{ plus } 1)\ln(d_i \text{ plus } 1)]n$$

where P is the population density per mg rhizosphere soil, d is the root depth and n is the total root length.

Experimental Results

Figure 2A:
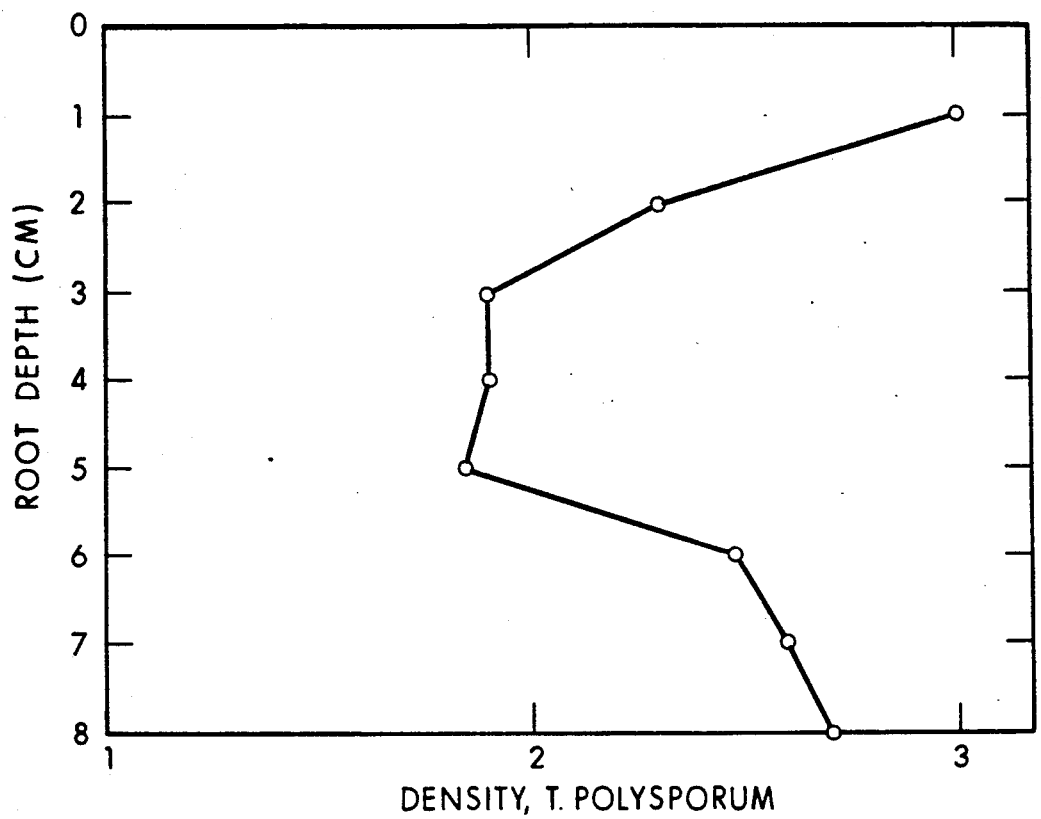
FIGS. 2A and 2B depict the population densities of Trichoderma spp. in the rhizosphere soil of cucumber plants without benomyl added to the soil.
Figure 2B:
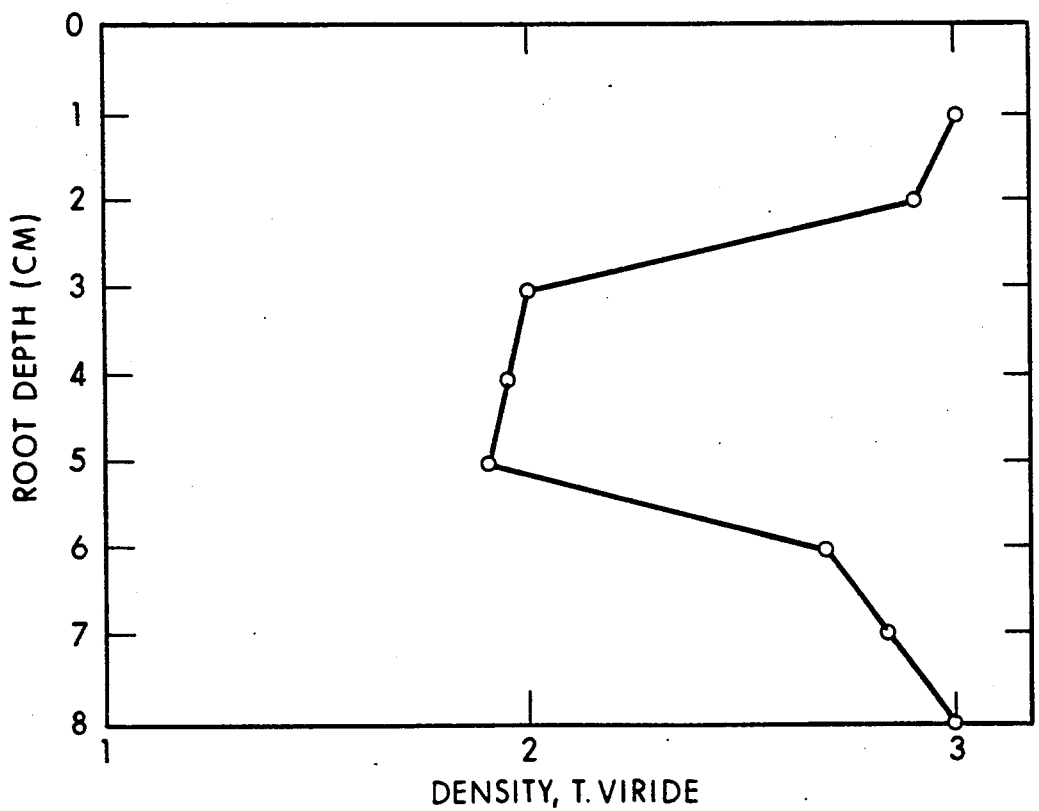
Figure 3:
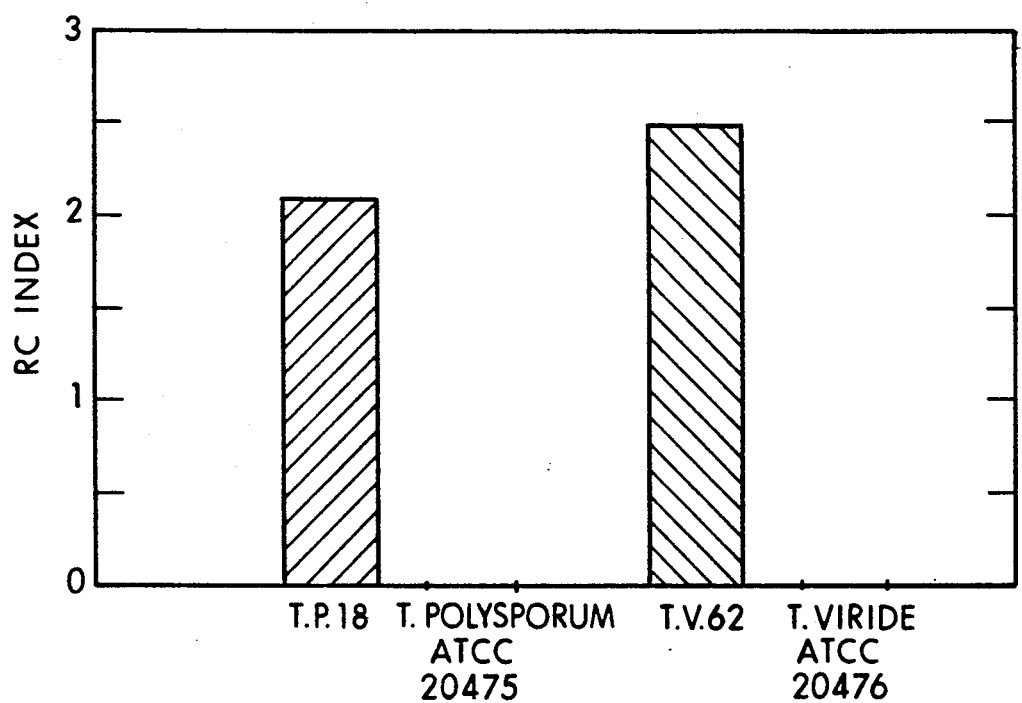
FIG. 3 is a bar graph depicting the rhizosphere competence (RC) index of *T. polysporum* T. P. 18, *T. viride* ATCC 20476, and *T. viride* T. V. 62.

Isolation of Trichoderma spp from rhizosphere soil. When cucumber seeds were treated with conidia and grown in pH 7.0 soil at 26° C., *T. polysporum* (ATCC 20475) and *T. viride* (ATCC 20476) were not detected in the rhizosphere soil at any depth, see FIGS. 2A-2B. On the other hand, *T. polysporum* (ATCC 20852) and *T. viride* (ATCC 20853) were isolated from the rhizosphere soil at all depths. The rhizosphere-competence (RC) index of each strain, as calculated by the equation, is shown in FIG. 3. The two mutants, *T. polysporum* (ATCC 20852) and *T. viride* (ATCC 20853) had RC indexes 2 and 2.5 whereas, both wild types *T. polysporum* (ATCC 20475) and *T. viride* (ATCC 20476) had zero values.

Tolerance to benomyl. *T. polysporum* (ATCC 20475) and *T. viride* (ATCC 20476) are not tolerant to benomyl. The mutation of these species by the mutagen, mentioned above, and selection on Trichoderma-selective medium has resulted in *T. polysporum* (ATCC 20852) and *T. viride* (ATCC 20853) tolerant to at least 10 mg/ml a.i. benomyl.

Growth of the subject Trichoderma spp. in liquid culture. When each of the subject strains of Trichoderma spp. were grown in Czapek Dox broth with cellulose as the sole source of carbon, the mutant mycelium attained significantly higher dry weight than all other wild type strains (FIG. 1).

Discussion

Although some biological control agents may protect seeds from soilborne pathogens, they do not proliferate in the rhizoplane and rhizosphere. Our experimental results indicates that strains of rhizosphere-incompetent biological control agents, *T. polysporum* (ATCC 20475) and *T. viride* (ATCC 20476) were induced to become rhizosphere-competent. Hence these Rhizosphere-competent biological control agents are potentially more effective because they protect not only the seed but also the root. Hence, they have the potential to eliminate the problem of adding large amounts of thalli to induce suppressiveness because substrates provided by the plant root can support their activity.

The pattern of hydrolytic enzymes used by strains of Trichoderma spp. for the hydrolysis of cellulose has been well studied. Exo and endo B-1,4-glucanases act on cellulose that has been broken down to cellobiose to glucose. Cellobiose is further hydrolyzed by, B-1,4-glucosidases to glucose. The mutants disclosed herein produce greater amounts of B-1,4-glucanases and B-1,4-glucosidases and utilize the cellulose substrate more efficiently. This is evident from the dry weight of mycelium produced. The mutants with higher cellulose activity than wild types can utilize cellulose substrates on or near the root more efficiently and thus, are rhizosphere-competent. Utilization of cellulose substrates is not associated with parasitism since microscopic examination revealed no evidence of such a relationship. A more likely source of cellulosic substrates is the remains of the primary cell wall in the mucigel surrounding the root. Hence, taken in total, our results indicate that *Trichoderma polysporum*, ATCC 20852 and *Trichoderma viride*, ATCC 20853 are each rhizosphere-competent and therefore may be used as biocontrol agents.

Thus having disclosed our invention, we claim:

1. A rhizosphere competent biocontrol agent, said biocontrol agent comprising *Trichoderma polysporum* ATCC 20852.

2. A rhizosphere competent biocontrol agent, said biocontrol agent comprising *Trichoderma viride* ATCC 20853.

* * * * *